United States Patent [19]

Shore et al.

[11] 4,349,522

[45] Sep. 14, 1982

[54] IRON, NICKEL AND COBALT TRI-OSMIUM CARBONYL HYDRIDES AND THEIR PREPARATION

[75] Inventors: Sheldon G. Shore, Columbus, Ohio; Jeffrey S. Plotkin, Heightstown, N.J.

[73] Assignee: The Ohio State University Research Foundation, Ohio

[21] Appl. No.: 275,693

[22] Filed: Jun. 22, 1981

Related U.S. Application Data

[63] Continuation-in-part of Ser. No. 150,228, May 15, 1980, abandoned.

[51] Int. Cl.$^3$ .................... C01G 49/16; C01G 55/00; C07F 15/00
[52] U.S. Cl. .................................. 423/417; 423/418; 260/439 CY
[58] Field of Search .............................. 423/416–418; 260/439 CY

[56] References Cited

U.S. PATENT DOCUMENTS 3,505,034  4/1970  L'Eplattenier et al. ........ 423/418 X

OTHER PUBLICATIONS

Deeming et al., "Addition Reactions of Polynuclear Osmium Hydrido Compound leading to Associative Carbonyl Substitution and Catalytic Alkene Isomerization", Journal of Organometallic Chemistry, 114 (1976) pp. 313–324.

Keister et al., "The Interaction of $H_2Os_3(CO)_{10}$ with Alkenes, Intermediates in Hydrogenation and Carbon–Hydrogen Bond Activation", J.A.C.S., 98:4, pp. 1056–1057 (1976).

Ferrari et al., "Cleavage of Carbon–Hydrogen Bonds in Reactions of Dodecacarbonyltriosmium with Pentenes and Hexenes", Inorganica Chimica Acta, vol. 20, (1976), pp. 141–143.

Moss et al., "A New route to mixed-metal carbonyls containing osmium", Journal of Organometallic Chemistry, 23 (1970), pp. C23–C24.

Geoffroy et al., "Synthesis of Tetrahedral Mixed-Metal Clusters of the Iron Triad. Preparation and Characterization of $H_2FeRu_2Os(CO)_{13}$ and $H_2FeRuOs_2(CO)_{13}$" J.A.C.S., 99 (1977), pp. 7565–7573.

Primary Examiner—Earl C. Thomas
Attorney, Agent, or Firm—Millard & Cox

[57] ABSTRACT $H_2Os_3(CO)_{10}$ has apparent Lewis base character and can be made to react with electron deficient iron, cobalt and nickel carbonyls, including salts of $[Fe(CO)_4]^{2-}$, $Fe_2(CO)_9$, $(\eta^5-C_5H_5)Co(CO)_2$, $Co_2(CO)_8$ and $[(\eta^5-C_5H_5)Ni(CO)]_2$, to give heteronuclear tri-osmium carbonyl hydrides, some of which are new compounds. New compounds disclosed include $H_2Fe_2Os_3(CO)_{16}$, $H_2Fe_2Os_3(CO)_{15}$, $H_2(\eta^5-C_5H_5)CoOs_3(CO)_{10}$ and $H_3(\eta^5-C_5H_5)NiOs_3(CO)_9$.

63 Claims, No Drawings

IRON, NICKEL AND COBALT TRI-OSMIUM CARBONYL HYDRIDES AND THEIR PREPARATION

The Government has rights in this invention pursuant to grant CHE-76-18705 awarded by the National Science Foundation.

CROSS-REFERENCE TO RELATED APPLICATIONS

This application is a continuation-in-part of our copending application Ser. No. 150,228 filed May 15, 1980 and now abandoned.

This application is cross-referenced to the commonly assigned application of Sheldon G. Shore, Donna G. Alway, and Jeffrey S. Plotkin entitled "Di-Iron Tri-Osmium Carbonyl Hydride Compound and Its Preparation", U.S. Ser. No. 150,229, filed May 15, 1980 now U.S. Pat. No. 4,282,312, the disclosure of which is expressly incorporated herein by reference.

BACKGROUND OF THE INVENTION

The present invention relates to mixed-metal carbonyl cluster compounds and more particularly to improved synthesis routes for their preparation and to novel mixed-metal carbonyl cluster compounds.

$H_2FeOs_3(CO)_{13}$ was first isolated by Moss and Graham, *J. Organomet. Chem.* 23, C23–C24 (1970), as a by-product in 6% yield from the reaction between $H_2Os(CO)_9$ and $Fe_2(CO)_9$. Subsequently, Geoffroy and Gladfelter, *J. Am. Chem. Soc.*, 99, 7565–7573 (1977), found that the reaction between the electron precise cluster $Os_3(CO)_{12}$ and $Fe(CO)_4{}^{2-}$ followed by protonation gave $H_2FeOs_3(CO)_{13}$ in 9% yield.

Other tri-osmium chemistry can involve the addition of nucleophilic organometallic reagents to the electronically unsaturated hydrido-osmium carbonyl cluster $H_2Os_3(CO)_{10}$ as a pathway to larger transition metal clusters. Such addition exploits the Lewis acid character of the tri-osmium system as exemplified by Stone and co-workers finding that certain electron rich $d^8$ and $d^{10}$ metal complexes will add to $H_2Os_3(CO)_{10}$ to yield a number of new heteronuclear transition metal clusters. Farrugia et al., *J. Chem. Soc. Chem. Comm.*, 260 (1978). For further studies on $H_2Os_3(CO)_{10}$, reference is made to the following: Keester et al., *JACS*, 98:4, 1056–1057 (1976); Deeming et al., *J. Organometal Chem.*, 114, 313–324 (1976); and Ferrari et al., *Inorganica Chemicta Acta*, 20, 141–143 (1976).

We have now discovered that, besides the previously-mentioned Lewis acid character, $H_2Os_3(CO)_{10}$ also possesses apparent Lewis base character and that this Lewis base character of $H_2Os_3(CO)_{10}$ may be used to provide new heteronuclear bimetallic cluster compounds and new pathways for the high yield synthesis of $H_2FeOs_3(CO)_{13}$, and other known heteronuclear bimetallic cluster compounds.

BROAD STATEMENT OF THE INVENTION

The invention provides a method for making a tri-osmium heteronuclear metal carbonyl compound, which comprises establishing a reaction mixture comprising an electron deficient metal carbonyl or carbonyl anion, in particular a cobalt, nickel or iron carbonyl or carbonyl anion, $H_2Os_3(CO)_{10}$ and a solvent which at least partially solubilizes at least one of the electron deficient compound and the $H_2Os(CO)_{10}$, the $H_2Os_3(CO)_{10}$ reacting with the electron deficient carbonyl compounds as a Lewis acid, and recovering the tri-osmium heteronuclear metal carbonyl compound from the reaction mixture.

The term "electron deficient metal carbonyl or carbonyl anion" as used herein includes not only those carbonyls and carbonyl anions which are truly electron-deficient (such as $Co_2(CO)_8$) but also those carbonyls and carbonyl anions which are not electron deficient in the normal sense but which will disproportionate to yield an electron deficient disproportionation product (for example $Fe_2(CO)_9$, which can be made to disproportionate to $Fe(CO)_5$ and the electron deficient $Fe(CO)_4$).

The solvent used in the instant method is desirably one which solubilizes both the electron deficient carbonyl or carbonyl anion and the $H_2Os_3(CO)_{10}$.

Examples of reactions which may be conducted by this method are as follows:

|   | Electron deficient carbonyl compound | Heteronuclear tri-osmium product(s) |
|---|---|---|
| A | $[Fe(CO)_4]^{2-}$ salt | $H_2FeOs_3(CO)_{13}$ and $H_2Fe_2Os_3(CO)_{16}*$ |
| B | $Fe_2(CO)_9$ | $H_2FeOs_3(CO)_{13}$ and $H_2Fe_2Os_3(CO)_{15}*$ |
| C | $(\eta^5\text{-}C_5H_5)Co(CO)_2$ | $H_2(\eta^5\text{-}C_5H_5)CoOs_3(CO)_{10}*$ |
| D | $Co_2(CO)_8$ | $HCoOs_3(CO)_{13}$ and $H_3CoOs_3(CO)_{12}$ |
| E | $[(\eta^5\text{-}C_5H_5)Ni(CO)]_2$ | $H_3(\eta^5\text{-}C_5H_5)NiOs_3(CO)_9*$ and a by-product * showing no hydride resonances in its proton magnetic resonance spectrum. |

The compounds marked * in the above table are novel and the invention extends to these novel compounds per se.

DETAILED DESCRIPTION OF THE INVENTION

As noted above, prior transition metal cluster chemistry involving the electronically unsaturated hydrido-osmium carbonyl cluster, $H_2Os_3(CO)_{10}$, relied on the Lewis acid character of the tri-osmium system. A significant discovery made during work on the present invention is that under proper reaction conditions, the same tri-osmium cluster can function as an apparent Lewis base. Utilizing this dual functionality of the tri-osmium cluster permits the synthesis of new mixed-metal cluster compounds in relatively high yields.

Preferred solvents for use in the instant method are aromatic solvents, ether solvents and chlorohydrocarbon solvents, the exact choice of solvents depending of course on the particular electron deficient carbonyl compound being used. Preferably the molar ratio of the electron deficient carbonyl compound to the $H_2Os_3(CO)_{10}$ is at least about stoichiometric. The electron deficient carbonyl compound may if desired be generated in situ in the reaction mixture for reaction with the $H_2Os_3(CO)_{10}$.

Many of the tri-osmium heteronuclear complexes produced by the instant method are sensitive to molecular oxygen and/or water. Accordingly, in most cases it is desirable to establish the reaction mixture in the substantial absence of molecular oxygen and water, usually under an inert gas blanket.

Specific preferred conditions for each of the five specific reactions tabulated above will now be discussed, the reactions being identified by the electron deficient starting material:

A [Fe(CO)$_4$]$^{2-}$ salt

The reactants are placed in a solvent which at least partially solubilizes the [Fe(CO)$_4$]$^{2-}$ salt for generation of [Fe(CO)$_4$]$^{2-}$. The [Fe(CO)$_4$]$^{2-}$ salt is only partially soluble in almost any solvents, although as the dianion reacts in the process, more of its salt is solubilized for reaction. Preferred solvents for use in this reaction include ethers and preferably those ethers which are relatively volatile for ease in separating the desired H$_2$FeOs$_3$(CO)$_{13}$ product during a later step of the process. Appropriate ethers include tetrahydrofuran, dimethyl ether, diethyl ether, glymes, and the like. Additional candidate solvents which may find some utility in the reaction include amines such as liquid ammonia and trialkyl amines, provided that they are unreactive with the reactants in the system and adequately solubilize the [Fe(CO)$_4$]$^{2-}$ salt for generation of the corresponding dianion.

The [Fe(CO)$_4$]$^{2-}$ salt is reacted with H$_2$Os$_3$(CO)$_{10}$ preferably in equimolar proportions, although an excess of either reactant may be used at the expense of such excess reactant. A variety of cations may be associated with the [Fe(CO)$_4$]$^{2-}$ salt as is readily apparent to those skilled in this art. Preferable cations include alkali metals such as, for example, potassium, lithium, sodium, cesium and rubidium, with potassium being the preferred cation of choice. Alternatively, a variety of other cations can be associated with the [Fe(CO)$_4$]$^{2-}$ and such compounds include amines (e.g. [(Ph)$_3$P]$_3$N+, where Ph is a phenyl group), tetraalkyl phosphoniums, tetraalkyl ammoniums, tetraphenyl phosphoniums, tetraphenyl ammoniums, and the like and mixtures thereof. Preparation of the [Fe(CO)$_4$]$^{2-}$ salt for entry into the reactions of the present invention is conventional.

The temperature of the reaction mixture is maintained at about 0° C. or lower, as at temperatures approaching about room temperature significant decomposition of reactants in the reaction mixture is experienced. Further, for suppressing degradation products in the reaction, the reaction mixture is maintained under conditions substantially free of molecular oxygen and water. Suitably, then, the reaction may be run under vacuum or under an inert gas, e.g. nitrogen, blanket as is necessary, desirable, or convenient.

Upon completion of this reaction, the reaction mixture then is combined with a protic acid to form the H$_2$FeOs$_3$(CO)$_{13}$ product. It should be noted that the use of excess [Fe(CO)$_4$]$^{2-}$ salt may mean that small quantities thereof may be insoluble in the volume of solvent chosen, but then monitoring the disappearance of the insoluble [Fe(CO)$_4$]$^{2-}$ salt generally will indicate when the reaction is complete. For this protonation step of the process, aqueous acids may be used as no apparent decomposition by-products have been noted when using aqueous protic acids. Suitable protic acids include, for example, hydrochloric acid, phosphoric acid, hydrobromic acid, and the like and mixtures thereof. Additionally, air may be contacted for brief periods with the reaction mixture during the protonation step of the process, though preferably the protonation step of the process is practiced under conditions substantially free of molecular oxygen (air). It should be noted additionally, that the solvent used in the first step of the process can be removed from the reaction mixture prior to the ptotonation step. The process produces H$_2$FeOs$_3$(CO)$_{13}$ as its major product but also produces the novel by-product H$_2$Fe$_2$Os$_3$(CO)$_{16}$ in low yields. Upon completion of the protonation step of the process, the desired orange-brown H$_2$FeOs$_3$(CO)$_{13}$ cluster product and the orange H$_2$Fe$_2$Os$_3$(CO)$_{16}$ cluster product may be separated from the reaction mixture by conventional techniques such as, for example, thin-layer chromatography.

Yields of the H$_2$FeOs$_3$(CO)$_{13}$ cluster product generally range from about 20% to 30% utilizing this process, this being much higher than the yields available from prior art processes. The orange-brown iron-osmium cluster can be identified on the basis of mass spectral data and its IR spectrum as compared to a previously reported spectrum. Additionally, analysis of the cluster shows that the 90 MHz $^1$H NMR spectrum consists of a single resonance at $-30.7$ $\tau$. This chemical shift value is as expected for metal edge bridging hydrides. The spectral identification of H$_2$Fe$_2$Os$_3$(CO)$_{16}$ will be given in Example 4 below.

B Fe$_2$(CO)$_9$

This particular reaction is only a one-step reaction as no protonation is required for production of the desired product. Preferred solvents for use in the reaction mixture are those which solubilize at least the H$_2$Os$_3$(CO)$_{10}$, especially aromatic solvents with benzene being especially preferred. Other suitable solvents include ethers which provide faster rates of reaction than do the aromatic solvents, though some loss of yield may be experienced. Amines are another class of solvents which may be useful in this process, though this is presently unconfirmed. Reaction temperatures for this process can range up to as high as about room temperature (25° C. for present purposes) which is the preferred temperature for conducting this reaction. Some decomposition is experienced at temperatures above room temperature and temperatures significantly below room temperature retard the reaction rate. Reaction conditions include the substantial absence of water in the reaction mixture and preferably the substantial adsence of oxygen (air), though little decomposition has been noted in the presence of oxygen.

The reaction mixture should contain the Fe$_2$(CO)$_9$ and the H$_2$Os$_3$(CO)$_{10}$ in a molar ratio of at least about 1:1 respectively. Generally an excess of the iron carbonyl will be used because side reactions lower the osmium yield from the reaction. Preferably a 2:1 molar ratio of the iron cluster to the tri-osmium cluster is maintained in the reaction mixture. Upon completion of the reaction, the H$_2$FeOs$_3$(CO)$_{13}$ product is separated from the reaction mixture. Yields of H$_2$FeOs$_3$(CO)$_{13}$ in this reaction generally exceed 80%, which is a substantial increase in yield compared to prior art synthesis schemes.

This reaction has already been stated to involve the apparent Lewis base functionality of the tri-osmium compound. Since it has been previously shown that in the presence of Lewis bases, (L), Fe$_2$(CO)$_9$ will fragment into Fe(CO)$_5$ and (CO)$_4$Fe(L), a proposed scheme for the formation of H$_2$FeOs$_3$(CO)$_{13}$ by this reaction is as follows:

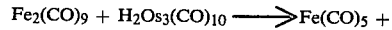

Fe$_2$(CO)$_9$ + H$_2$Os$_3$(CO)$_{10}$ ⟶ Fe(CO)$_5$ +

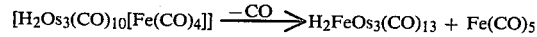

[H$_2$Os$_3$(CO)$_{10}$[Fe(CO)$_4$]] $\xrightarrow{-CO}$ H$_2$FeOs$_3$(CO)$_{13}$ + Fe(CO)$_5$ It should be noted that small quantities of a new red compound also are formed during this reaction. Mass spectral data indicates that this new material is a pentanuclear cluster having the molecular formula $H_2Fe_2Os_3(CO)_{15}$. It should be noted that this new pentanuclear cluster is an apparent isomer of the pentanuclear cluster disclosed in the commonly assigned application of Shore et al, U.S. Ser. No. 150,229 now U.S. Pat. No. 4,282,197. The following spectral data identifies the two isomers of $H_2Fe_2Os_3(CO)_{15}$ as disclosed herein and in U.S. Ser. No. 150,229:

| Characteristic | U.S.S.N. 150,229 | Present Invention |
| --- | --- | --- |
| Mass Spec. | $\frac{m}{e} = 1110$(cut-off) | $\frac{m}{e} = 1108$(P-2) |
| Infrared Spectra, $\nu(CO)(cm^{-1})$ (cyclohexane, room temp.) | 2090(m),2075(s), 2040(m),2030(m), 2025(m),2005(m), 1998(m),1990(w) | 2110(w),2100(m),2082(s), 2070(s),2045(s),2038(m), 2020(s),2002(m),1990(w) 1985(sh) |
| Color: | Yellow | Red |

C ($\eta^5$-$C_5H_5$)Co(CO)$_2$

Preferred solvents are non-polar solvents and chief among these are the aromatic compounds including preferably toluene. Of course, other suitable solvents may be used provided that they adequately solubilize the reactants and are non-participating in the reaction. The reaction mixture is desirably established at a temperature ranging from about 60° to 120° C. with 90° C. being preferred for maximizing the yield of the desired product. While molecular oxygen (air) and water apparently do not cause significant degradation of reactants in the process, their exclusion is distinctly preferred. Since the cobalt reactant is somewhat volatile, a closed system is preferred for minimizing loss thereof. Accordingly, the reaction preferably is carried out under an inert gas blanket. Preferably, the molar ratio of the ($\eta^5$-$C_5H_5$)Co(CO)$_2$ to the $H_2Os_3(CO)_{10}$ in the reaction mixture is at least about 1:1 though higher proportions of cobalt to tri-osmium can be used.

After the reaction is completed $H_2(\eta^5$-$C_5H_5)CoOs_3(CO)_{10}$ is isolated from the reaction mixture. This new cobalt tri-osmium cluster is an air stable blackish-green material which can be recovered in about 60% yield. The mass spectrum of this material contains a cut-off of m/e 982 which is consistent with the molecular formula proposed. In addition, the peak intensities of the parent mass spectral envelope are as expected for tri-osmium system. The carbonyl region of the IR spectrum contains bands at (cyclohexane) 2095 cm$^{-1}$(m), 2068(vs), 2050 (vs), 2012(vs), 2000(sh), 1977 (m), 1968 (m), and 1800 (s). The PMR spectrum at $-80°$ C. consists of one sharp resonance of intensity five at 4.53$\tau$, attributable to the cyclopentadienyl ring, and two bands each of intensity one at 27.17$\tau$ and 30.89$\tau$, due to two non-equivalent edge bridging hydrides. Interestingly, it was noted that as the temperature of the cluster is raised, the hydride resonances broaden and at +22° C. these hydride resonances have coalesced into one weak broad peak centered at 29.03$\tau$; however, the cyclopentadienyl resonance remains virtually unchanged.

D Co$_2$(CO)$_8$

The solvent used in the reaction mixture is conveniently a chlorohydrocarbon, preferably methylene chloride. It is preferred to use at least one mole of Co$_2$(CO)$_8$ per mole of $H_2Os_3(CO)_{10}$ though more of the cobalt compound may be used if desired. The reaction mixture is desirably maintained at a temperature not above about room temperature, room temperature being the preferred temperature for carrying out the reaction.

As well as HCoOs$_3$(CO)$_{13}$, the reaction produces a minor proportion of $H_3CoOs_3(CO)_{12}$. Typical yields are 48% of HCoOs$_3$(CO)$_{13}$ and 9% of $H_3CoOs_3(CO)_{12}$. In both cases, these yields are much greater than those previously achieved in the synthesis of these known compounds. The two products may be separated by chromatography on silica gel using a hexane/benzene liquid phase.

E ([($\eta^5$-$C_5H_5$)Ni(CO)]$_2$

The solvent used in the reaction mixture is conveniently a chlorohydrocarbon, preferably methylene chloride. It is preferred to use at least one mole of [($\eta^5$-$C_5H_5$)Ni(CO)]$_2$ per mole of $H_2Os_3(CO)_{10}$ though more of the nickel compound may be used if desired. The reaction mixture is desirably maintained at a temperature in the range of about 60° to about 120° C. and preferably at about 90° C.

As well as the novel compound $H_3(\eta^5$-$C_5H_5)NiOs_3(CO)_9$, the reaction produces a minor proportion of a novel by-product the formula of which has not yet been determined, but which displays no hydride resonances in its proton magnetic resonance spectrum. Typical yields are 50% of $H_3(\eta^5$-$C_5H_5)NiOs_3(CO)_9$ and about 25% of the by-product. The two products may be separated by chromatography on silica gel using a hexane/benzene liquid phase. Further details of the spectra of the two products are given in Example 6 below.

The instant method is not restricted to the specific reactions (A)-(E) described in detail above but may be used for insertion of other transition metals into the tri-osmium framework. Such other pathways would involve the reaction of $H_2Os_3(CO)_{10}$ with an electron deficient (electrophilic) metal complex or intermediate complex. Such a system relies on the apparent Lewis base property or nucleophilicity of the tri-osmium cluster for synthesizing new heteronuclear metal clusters. While any metal could form the electron deficient metal complex, cobalt, iron, cobalt and nickel are preferred as the metal of the electron deficient complex. Similarly, such electron deficient species need not be carbonyl complexes, but carbonyl complexes are preferred. Suitable solvents would be those solvents disclosed herein which solubilize at least the tri-osmium reactant. It must be recognized that for each system the reaction conditions (eg. temperature, molar ratio of reactants, tolerance of water, tolerance of molecular oxygen, etc.) may vary somewhat, but determination of such reaction conditions should be routine based on the disclosure herein contained.

In view of the proven ability of $H_2Os_3(CO)_{10}$ and $Os_3(CO)_{12}$ to catalyze olefin isomerizations, the mixed-metal clusters of the present invention are expected to have potential catalytic activity. Such clusters may perhaps be chemically attached to supports to provide a heterogeneous catalyst system analogous to the systems described by Pierantozzi et al., *JACS*, 101:18, 5436–5438 (1979). Further, such supported cluster compounds even may have further utility by their reduction on the support to produce new bi-metallic metal catalyst candidates having unique surface properties. Further on this can be found by reviewing McVicker and Vannice, "The Preparation, Characterization, and Use of Supported Potassium-group VIII Metal Complexes as Catalysts for CO Hydrogenation", Exxon Research and Engineering Company, Corporate Pioneering Research Laboratories, Linden, New Jersey (1979). Further data transition metal carbonyl cluster catalysts is disclosed by Basset and Smith in Abstracts of Invited Talks, XIX International Conference on Pure and Applied Chemistry, Prague, Czechosolvakia, pages 161–164 (1978). For a good discussion on cluster catalysis, reference is made to J. J. Bassett and R. Ugo, *Aspects of Homogeneous Catalysis*, Chapter 2, Vol. 3, D. Reidel, Dordrecht, Holland (1977). In particular, the heteronuclear tri-osmium complexes produced by the instant method are believed to be useful as Fischer-Tropsch catalysts.

The following examples show how the present invention can be practiced, but should not be construed as limiting. In this application, all units are in the metric system, unless otherwise expressly indicated. Also, all citations disclosed herein are expressly incorporated herein by reference.

EXAMPLE 1

Preparation of $H_2FeOs_3(CO)_{13}$ from $K_2Fe(CO)_4$

Equimolar quantities of $K_2Fe(CO)_4$ (0.13 mmole) and $H_2Os_3(CO)_{10}$ (0.13 mmole) were placed in a 50 ml round-bottom flask equipped with a greaseless stopcock and containing a magnetic stir bar. The flask was evacuated by a high vacuum line and then approximately 10 ml of THF (tetrahydrofuran) was condensed in at liquid nitrogen temperature. This solution then was warmed to 0° C. and magnetically stirred. Within minutes, the characteristic purple color of $H_2Os_3$-$(CO)_{10}$ was replaced by a deep red color. Stirring was continued for 20 hours to allow all of the excess insoluble $K_2Fe(CO)_4$ to be consumed.

The THF solvent then was removed under vacuum and several ml of anhydrous HCl were condensed in and stirred at −110° C. After one hour reaction time, excess HCl was removed and the flask opened to the air. The resulting orange-brown neutral material was chromatographed on a silica gel column. Elution with hexane gave small amounts of materials determined to be unreacted (purple) $H_2Os_3(CO)_{10}$ and green $Fe_3(CO)_{12}$. The major yellow-orange component was eluted with an 80/20 hexane/benzene solvent mixture. This material (36 mg., 28% yield) was identified as the previously known $H_2FeOs_3(CO)_{13}$ on the basis of mass, IR, and NMR spectral data.

EXAMPLE 2

Preparation of $H_2FeOs_3(CO)_{13}$ and $H_2Fe_2Os_3(CO)_{15}$ from $Fe_2(CO)_9$ A two-fold excess of $Fe_2(CO)_9$ was added to a benzene solution of $H_2Os_3$-$(CO)_{10}$ (74 mg). This reaction mixture was frozen and evacuated of air. After warming the mixture to room temperature, the mixture was stirred until all of the $H_2Os_3(CO)_{10}$ had been consumed. Consumption of $H_2Os_3(CO)_{10}$ can be monitored conveniently by periodic sampling of the reaction mixture by TLC. After about 20 hours reaction time, the reaction was determined to be complete and the system was opened to the air. Benzene solvent was removed by rotary evaporation and the remaining solid material dissolved in methylene chloride solvent, filtered, concentrated, and chromatographed on preparative TLC plates using an 80/20 hexane/benzene solvent system. Besides the expected $Fe_3(CO)_{12}$ by-product, two other iron-containing clusters were isolated. One of these clusters was $H_2FeOs_3(CO)_{13}$ (70 mg, 82% yield) and the other was a red compound (2 mg) which by mass spectral data was determined to be of the formula $H_2Fe_2Os_3(CO)_{15}$.

This example clearly shows the high yields which can be achieved by employing the Lewis base functionality of $H_2Os_3(CO)_{10}$ reactant in the preparation of mixed-metal carbonyl cluster compounds.

EXAMPLE 3

Preparation of $H_2(\eta^5\text{-}C_5H_5)CoOs_3(CO)_{10}$ from $(\eta^5\text{-}C_5H_5)Co(CO)_2$ Freshly distilled $(\eta^5\text{-}C_5H_5)Co(CO)_2$ (140 mg) was added to a 2-neck 50 ml flask and the flask evacuated of air. Approximately 8 ml of toluene was condensed in followed by the addition of 47 mg of $H_2Os_3(CO)_{10}$ under a stream of nitrogen gas. The solution was warmed to 90° C. and stirred until all of the $H_2Os_3$-$(CO)_{10}$ had been consumed. After 48 hours reaction time, the solvent and unreacted $(\eta^5\text{-}C_5H_5)Co(CO)_2$ were removed from the reaction mixture. The remaining dark green solid material was dissolved in methylene chloride and chromatographed on preparative silica gel TLC plates. Elution with 80/20 hexane/benzene solvent mixture yielded one major dark green band-35 mg or 60% yield of $H_2(\eta^5\text{-}C_5H_5)CoOs_3(CO)_{10}$. This cluster was characterized on the basis of its spectroscopic behavior as described above.

EXAMPLE 4

Preparation of $H_2FeOs_3(CO)_{13}$ and $H_2Fe_2Os_3(CO)_{16}$ from $K_2Fe(CO)_4$ $K_2Fe(CO)_4$ (0.1211 g; 0.492 mmole) was placed in a tip-tube under nitrogen. The tip-tube was attached to a nitrogen filled 100 ml two-neck round bottom flask containing $H_2Os_3(CO)_{10}$ (0.4188 g; 0.492 mmole). The flask was evacuated on a high vacuum line. Approximately 20 ml of THF (distilled from $LiAlH_4$, stored over Na/benzophenone) was condensed into the flask at −78° C. The solution was warmed to room temperature and magnetically stirred until all of the $H_2Os_3(CO)_{10}$ had dissolved. The purple solution was cooled to 0° C., and the $K_2[Fe(CO)_4]$ added. The solution was stirred at 0° C. for 24 hours, after which time no non-condensable gases had formed. The solvent was removed under vacuum to leave an orange-brown oil. Approximately 10 ml of $CH_2Cl_2$ (distilled from $LiAlH_4$) which contained 0.984 mmole of HCl was condensed into the flask at −196° C. The solution was stirred at −78° C. for two hours and then at room temperature for two hours. A total of 0.10 mmole of non-condensable gas was produced. Mass spectral analysis revealed the gaseous composition to be 94% $H_2$ and 6% CO. A brown precipitate settled out of the red-brown solution. The $CH_2Cl_2/HCl$ was removed under vacuum and approximately 20 ml fresh $CH_2Cl_2$ was condensed into the flask at −78° C. The brown solution was filtered from the brown powder (0.17 g obtained). The solvent was removed from the filtrate under vacuum to leave a brown oil. The oil was exposed to air, dissolved in approximately 40 ml hexane, and chromatographed on a 3.5×30 cm column of 100–200 mesh silica gel.

Elution with hexane gave a purple band which was identified as unreacted $H_2Os_3(CO)_{10}$ by infrared spectroscopy. 33 mg (8% of the starting amount) was recovered. A green band identified as $Fe_3(CO)_{12}$ by infrared spectroscopy, eluted second. This band was followed by an unidentified red-purple component. An orange band that remained at the top of the column was eluted with $CHCl_3$. The $CHCl_3$ was removed by rotary evaporation to leave and orange solid. The solid was dissolved in approximately 5 ml $CH_2Cl_2$, and its components separated by thin layer chromatography on a silica gel plate (20×20 cm, 0.5 cm thick) using 80/20 hexane/benzene as elutant. A yellow component, identified as $H_2FeOs_3(CO)_{13}$ by infrared analysis, was eluted. An orange band followed. The solvent was removed from this orange fraction to yield 8 mg of an orange powder, characterized as $H_2Fe_2Os_3(CO)_{16}$ by mass spectral analysis (1% yield).

The spectral data on this new pentanuclear cluster, $H_2Fe_2Os_3(CO)_{16}$ is given below.

Mass Spectral Data: $H_2Fe_2Os_3(CO)_{16}$: calculated (m/e)=1137.68765; observed (m/e)=1137.68967

Infrared Spectral Data (cyclohexane solution):
$\nu(CO)$ $(cm^{-1})$ 2086(vs), 2070(vs), 2062(vs), 2041(w), 2031(s), 2005(m), 1983(w).

$^1H$ NMR Spectral Data ($CDCl_3$ solution): $\delta = -21.4$ ppm.

EXAMPLE 5

Preparation of $HCoOs_3(CO)_{13}$ and $H_3CoOs_3(CO)_{12}$ from $Co_2(CO)_8$ 0.25 g. of $H_2Os_3(CO)_{10}$ (0.293 mmole.) and 0.1 g. of $Co_2(CO)_8$ (0.293 mmole.) were placed in a two-necked round-bottomed flask and brought to a temperature of −78° C. About 20 ml of methylene chloride (distilled from phosphorus pentoxide) was condensed into the flask. After degasing by two freeze-pump-thaw cycles, the resultant reaction mixture was warmed to room temperature and magnetically stirred at this temperature for 50 hours, after which time a total of 0.28 mmoles of non-condensible gas had been evolved.

The methylene chloride and small remaining amount of $Co_2(CO)_8$ (identified by its infrared spectrum) were removed from the reaction mixture under vacuum to leave a brown residue. This residue was dissolved in a 1:1 v/v benzene/hexane mixture and chromatographed on 75×35 cm. silica gel TLC plates. Elution with hexane gave a dark brown band, amounting to a total of 21 mg. after solvent removal, of a mixture identified by infrared spectroscopy as consisting of $Co_4(CO)_{12}$ and a small amount of $H_2Os_3(CO)_{12}$. An orange band that remained at the top of the plate was eluted with a 1:4 v/v benzene/hexane mixture, whereupon a yellow band separated from a slower moving orange band. The yellow band amounted to 28 mg. after solvent removal and was shown by infrared spectroscopy and mass analysis (m/e=974) to be $H_3CoOs_3(CO)_{12}$. The orange band was eluted and the solvent removed by rotary evaporation to leave an orange-red powder which was recrystallized from methylene chloride/hexane at −10° C. to afford 0.14 g. of orange-red crystals characterized by infrared, mass and proton magnetic resonance spectroscopy as $HCoOs_3(CO)_{13}$ (48% yield).

High-precision mass spectroscopy gave a m/e value=1000, in exact agreement with the calculated value. The infrared spectrum shown bands at 2118(w), 2080(s), 2060(vs), 2040(m), 2030(m,sh), 2010(m,sh), 1995(m), 1986(w) and 1855(m) $cm^{-1}$. The proton magnetic resonance spectrum in methylene chloride at room temperature, which has not previously been reported, showed a single band at $\tau = 30.28$. The proton magnetic resonance spectrum in methylene chloride shows a singlet at $\tau = 20.28$ p.p.m. relative to tetramethylsilane. The $^1H$-decoupled $^{13}C$ nuclear magnetic resonance spectrum in methylene chloride at room temperature shows peaks at 213.5, 210.7, 189.6, 174.0, 173.6, 173.1 and 164.9 p.p.m. relative to tetramethylsilane.

The above spectral data suggests a structure having two bridging carbonyls and one Os-Os bridged hydride. The suggested structure of the compound has the metal atoms arranged at the corners of a tetrahedron, three carbonyls being coordinated with each osmium atom, one carbonyl being coordinated with the cobalt atom, the last three carbonyls bridging differing Co-Os edges and the hydride bridging one Os-Os edge.

EXAMPLE 6

Preparation of $H_3(\eta^5\text{-}C_5H_5)NiOs_3(CO)_9$ and a non-hydride by-product from $[(\eta^5\text{-}C_5H_5)Ni(CO)]_2$ 50 mg. of $H_2Os_3(CO)_{10}$ (0.059 mmoles) and 18 mg. of $[(\eta^5\text{-}C_5H_5)Ni(CO)]_2$ (0.059 mmoles) were placed in a two-necked 30 ml. reaction vessel and cooled to −78° C. About 15 ml. of toluene (distilled from lithium aluminum hydride) was condensed into the reaction vessel at this temperature and, after degasing by two freeze-pumpthaw cycles, the reaction mixture was warmed to 90° C. and magnetically stirred at this temperature for 10 hours. Infrared spectra showed the complete disappearance of both the osmium and nickel carbonyl starting materials. The solvent was removed under reduced pressure from the reaction mixture to leave a purple-brown residue, which was dissolved in about 5 ml. of methylene chloride and subjected to thin layer chromatography on silica gel plates of 0.5 mm. thickness using a 1:4 v/v benzene/hexane mixture as elutant. Two major bands were developed, a purple band having a relatively high $R_f$ value and a dark brown band having a lower $R_f$ value. These two bands were separately scraped off the plate, eluted with methylene chloride and the solvent removed by rotary evaporation. The purple band produced 32.4 mg (50.3% based on $H_2Os_3(CO)_{10}$) of $H_3(\eta^5\text{-}C_5H_5)NiOs_3(CO)_9$.

Elemental analysis yielded the following results: $H_3(\eta^5\text{-}C_5H_5)NiOs_3(CO)_9$: Calc: C, 17.71; H, 0.85; Ni 6.18; Os, 60.09. Found: C, 17.48; H, 0.73; Ni 6.15; Os 60.91.

High resolution was spectroscopy on the m/e 954 parent peak confirmed an elemental composition of $^1H_8$ $^{12}C_{14}$ $^{16}O_9$ $^{58}Ni$ $^{191}Os_3$ (observed 953.8382, calculated 953.8357. Infrared spectroscopy in hexane gave carbonyl peaks at 2085 (vw), 2065(s), 2010(vs) and 1990(w) $cm^{-1}$. Proton magnetic resonance in deuterochloroform at room temperature showed singlets at $\delta = 6.05$ (5H) and −17.65 (3H) p.p.m. relative to tetramethylsilane and the $^1H$-coupled 75.5 MHz $^{13}C$ nuclear magnetic resonance spectrum in methylene chloride at room temperature showed a doublet at 87.0 p.p.m. with $J_{CH} = 188.8$ Hz, attributed to cyclopentadienyl carbons, a doublet at 171.7 p.p.m. with $J_{CH} = 7.8$ Hz, attributed to equatorial terminal carbonyl and a singlet at 179.4 p.p.m. attributed to axial terminal carbon (all relative to tetramethylsilane). Both the doublets collapsed to singlets in the $^1H$-decoupled $^{13}C$ spectrum and no temperature effect was observed on either the $^1H$ or the $^{13}C$ nuclear magnetic resonance spectrum from $-80°$ C. to room temperature. Based upon these spectral data, the compound is believed to have a structure in which the metal atoms from a tetrahedron, three carbonyls being coordinated with each osmium atom, a hydride ion bridging each Os-Os edge and the cyclopentadienyl ligand being coordinated with the nickel atom.

The dark brown band produced 20 mg. of a dark brown powder showing infrared bands in hexane at 2058(w), 2036(w), 2020(vw), 2010(s), 1987(w), 1975(m,sh), 1966(s) and 1955(m,sh) $cm^{-1}$. The dark brown powder showed no protons in the hydride region of the proton magnetic resonance spectrum. Treatment of this compound with hydrogen gas by slowly bubbling prepurified hydrogen through a toluene solution of the compound at 90° C. for 12 hours gave a purple mixture shown by infrared spectroscopy to contain $H_3(\eta^5-C_5H_5)NiOs_3(CO)_9$ and other unidentified compounds.

We claim:

1. A method for making a tri-osmium heteronuclear metal carbonyl compound, which comprises:
    (a) establishing a reaction mixture comprising an electron deficient cobalt, nickel or iron carbonyl or carbonyl anion, $H_2Os_3(CO)_{10}$, and a solvent which at least partially solubilizes at least one of said electron deficient carbonyl compound and said $H_2Os_3(CO)_{10}$, said $H_2Os_3(CO)_{10}$ reacting with said electron deficient carbonyl compound as a Lewis base; and
    (b) recovering said tri-osmium heteronuclear metal carbonyl compound from said reaction mixture.

2. A method according to claim 1 wherein said solvent solubilizes both said electron deficient carbonyl compound and said $H_2Os_3(CO)_{10}$.

3. A method according to claim 1 wherein said solvent is an aromatic solvent, an ether solvent, or a chlorohydrocarbon solvent.

4. A method according to claim 1 wherein the molar ratio of said electron deficient carbonyl compound to said $H_2Os_3(CO)_{10}$ is at least about stoichiometric.

5. A method according to claim 1 wherein said electron deficient carbonyl compound is generated in said reaction mixture for reaction with said $H_2Os_3(CO)_{10}$.

6. A method according to claim 1 wherein said reaction mixture is established in the substantial absence of molecular oxygen and water.

7. A method according to claim 6 wherein said reaction mixture is established under an inert gas blanket.

8. A method according to claim 1 wherein said electron deficient carbonyl compound is a salt of $[Fe(CO)_4]^{2-}$ and said tri-osmium heteronuclear metal carbonyl compound produced is $H_2FeOs_3(CO)_{13}$ and/or $H_2Fe_2Os_3(CO)_{16}$.

9. A method according to claim 8 wherein:
    (a) said reaction mixture comprising a salt of $[Fe(CO)_4]^{2-}$, $H_2Os_3(CO)_{10}$, and a solvent which at least partially solubilizes said $[Fe(CO)_4]^{2-}$ salt to generate a $[Fe(CO)_4]^{2-}$ dianion is established under conditions substantially free of molecular oxygen and water, and at a temperature not substantially above about 0° C.; and
    (b) a protic acid is added to said reaction mixture to form said $H_2FeOs_3(CO)_{13}$.

10. A method according to claim 9 wherein the cation of said $[Fe(CO)_4]^{2-}$ salt is an alkali metal, a tetraalkyl or tetraaryl phosphonium, a tetraalkyl or tetraaryl quaternary ammonium, or an amine.

11. A method according to claim 10 wherein said cation is potassium or $[(Ph)_3P]_2N^+$, where Ph is a phenyl group.

12. A method according to claim 9 wherein said solvent is an ether.

13. A method according to claim 12 wherein said solvent is tetrahydrofuran, dimethyl ether, dimethyl ether, or a glyme.

14. A method according to claim 9 wherein the molar ratio of said $[Fe(CO)_4]^{2-}$ dianion to said $H_2Os_3(CO)_{10}$ is about 1:1.

15. A method according to claim 9 wherein said reaction mixture is established under an inert gas blanket.

16. A method according to claim 9 wherein said protic acid addition is conducted in the presence of molecular oxygen and water.

17. A method according to claim 9 wherein said protic acid addition is conducted in the substantial absence of molecular oxygen and water.

18. A method according to claim 9 wherein said protic acid is HCl, HBr, $H_2SO_4$, or $H_3PO_4$.

19. A method according to claim 9 wherein $H_2Fe_2Os_3(CO)_{16}$ is also separated from said reaction mixture.

20. A method according to claim 19 wherein, after said protic acid addition, said reaction mixture is chromatographed on silica gel using a hexane/benzene liquid phase to separate said $H_2Fe_2Os_3(CO)_{16}$ from said $H_2FeOs_3(CO)_{13}$.

21. A method according to claim 1 wherein said electron deficient carbonyl compound is $Fe_2(CO)_9$ and said tri-osmium heteronuclear metal carbonyl compound produced is $H_2FeOs_3(CO)_{13}$ and/or $H_2Fe_2Os_3(CO)_{15}$.

22. A method according to claim 21 wherein:
    (a) said reaction mixture comprising $Fe_2(CO)_9$ and $H_2Os_3(CO)_{10}$ in a molar ratio of at least 1:1, respectively, and a solvent which solubilizes said $H_2Os_3(CO)_{10}$, is established under substantially anhydrous conditions at a temperature not substantially above about room temperature; and
    (b) said $H_2FeOs_3(CO)_{13}$ is separated from said reaction mixture.

23. A method according to claim 22 wherein said solvent is an aromatic solvent or an ether solvent.

24. A method according to claim 23 wherein said solvent is benzene.

25. A method according to claim 22 wherein the molar ratio of said $Fe_2(CO)_9$ to said $H_2Os_3(CO)_{10}$ is between about 1:1 and 2:1.

26. A method according to claim 22 wherein said reaction mixture is established in the substantial absence of molecular oxygen.

27. A method according to claim 22 wherein $H_2Fe_2Os_3(CO)_{15}$ is also recovered from said reaction mixture.

28. A method according to claim 27, wherein said reaction mixture is chromatographed on silica gel using a hexane/benzene liquid phase to separate said $H_2Fe_2Os_3(CO)_{15}$ from said $H_2FeOs_3(CO)_{13}$.

29. A method according to claim 1 wherein said electron deficient carbonyl compound is $(\eta^5-C_5H_5)Co(CO)_2$ and said tri-osmium heteronuclear metal carbonyl compound produced is $H_2(\eta^5-C_5H_5)CoOs_3(CO)_{10}$.

30. A method according to claim 29 wherein:
    (a) said reaction mixture comprising $(\eta^5-C_5H_5)Co(CO)_2$ and $H_2Os_3(CO)_{10}$ in a molar ratio of at least 1:1 respectively, and a non-polar solvent in which said cobalt and tri-osmium compounds are soluble is established at a temperature of between about 60° and 120° C.; and (b) said $H_2(\eta^5\text{-}C_5H_5)CoOs_3(CO)_{10}$ is recovered from said reaction mixture.

31. A method according to claim 30 wherein said solvent is an aromatic solvent.

32. A method according to claim 31 wherein said solvent is toluene.

33. A method according to claim 30 wherein said temperature is between about 85° and 95° C.

34. A method according to claim 30 wherein said reaction mixture is established in a closed reaction vessel and under an inert gas blanket.

35. A method according to claim 33 wherein said solvent is toluene.

36. A method according to claim 1 wherein said electron deficient carbonyl compound is $Co_2(CO)_8$ and said tri-osmium heteronuclear metal carbonyl compound produced is $HCoOs_3(CO)_{13}$ and/or $H_3CoOs_3(CO)_{12}$.

37. A method according to claim 36 wherein:
(a) said reaction mixture comprising $Co_2(CO)_8$ and $H_2Os_3(CO)_{10}$ in a molar ratio of at least about 1:1 respectively, and a non-polar solvent in which said cobalt and tri-osmium compounds are soluble is established at a temperature not substantially above about room temperature; and
(b) said $HCoOs_3(CO)_{13}$ is recovered from said reaction mixture.

38. A method according to claim 37 wherein said solvent is a chlorohydrocarbon.

39. A method according to claim 38 wherein said solvent is methylene chloride.

40. A method according to claim 37 wherein said reaction mixture is established in the substantial absence of molecular oxygen and water.

41. A method according to claim 37 wherein $H_3CoOs_3(CO)_{12}$ is also recovered from said reaction mixture.

42. A method according to claim 41 wherein said reaction mixture is chromatographed on silica gel using a hexane/benzene liquid phase to separate said $H_3CoOs_3(CO)_{12}$ from said $HCoOs_3(CO)_{13}$.

43. A method according to claim 1 wherein said electron deficient carbonyl compound is $[(\eta^5\text{-}C_5H_5)Ni(CO)]_2$ and said tri-osmium heteronuclear metal carbonyl compound produces is $H_3(\eta^5\text{-}C_5H_5)NiOs_3(CO)_9$.

44. A method according to claim 43 wherein:
(a) said reaction mixture comprising $[(\eta^5\text{-}C_5H_5)Ni(CO)]_2$ and $H_2Os_3(CO)_{10}$ in a molar ratio of at least about 1:1 respectively, and a non-polar solvent in which said nickel and tri-osmium compounds are soluble is established at a temperature between about 60° and 120° C.; and
(b) said $H_3(\eta^5\text{-}C_5H_5)NiOs_3(CO)_9$ is recovered from said reaction mixture.

45. A method according to claim 44 wherein said solvent is an aromatic solvent.

46. A method according to claim 45 wherein said solvent is toluene.

47. A method according to claim 44 wherein said reaction mixture is established in the substantial absence of molecular oxygen and water.

48. A method according to claim 44 wherein said reaction mixture is established at a temperature of about 85° C.

49. A method according to claim 44 wherein there is also recovered from said reaction mixture a by-product showing no hydride protons in its nuclear magnetic resonance spectrum but having infrared bands at about 2058, 2036, 2020, 2010, 1987, 1975, 1966 and 1955 $cm^{-1}$.

50. A method according to claim 49 wherein after removal of said solvent said reaction mixture is chromatographed on silica gel using a hexane/benzene liquid phase to separate said by-product from said $H_3(\eta^5\text{-}C_5H_5)NiOs_3(CO)_9$.

51. A product produced by the method of claim 1.
52. A product produced by the method of claim 8.
53. A product produced by the method of claim 21.
54. A product produced by the method of claim 29.
55. A product produced by the method of claim 36.
56. A product produced by the method of claim 43.
57. $H_2Fe_2Os_3(CO)_{16}$.
58. The $H_2Fe_2Os_3(CO)_{15}$ product of the process of claim 21.
59. The compound $H_2Fe_2Os_3(CO)_{15}$, characterized by being red in color, having a mass spectral m/e value of about 1108 (P-2), and infrared absorption peaks (cyclohexane solvent at room temperature) at about the following wave numbers [(CO), $cm^{-1}$] 2110, 2100, 2082, 2070, 2045, 2038, 2020, 2002, 1990, and 1985.

60. The compound $H_2Fe_2Os_3(CO)_{15}$, characterized as being capable of being made by the reaction of $Fe_2(CO)_9$ and $H_2Os_3(CO)_{10}$ in a molar ratio of about 2:1 in benzene solvent under substantially anhydrous conditions at a temperature of about 25° C.

61. $H_2(\eta^5\text{-}C_5H_5)CoOs_3(CO)_{10}$.
62. $H_3(\eta^5\text{-}C_5H_5)NiOs_3(CO)_9$.

63. A nickel carbonyl compound characterized as being capable of being made by the reaction of $(\eta^5\text{-}C_5H_5)Ni(CO)_2$ and $H_2Os_3(CO)_{10}$, as displaying no protons in the hydride region of its proton nuclear magnetic resonance spectrum and showing infrared bands at about 2058, 2036, 2020, 2010, 1987, 1975, 1966 and 1955 $cm^{-1}$.

* * * * *